US011879038B2

(12) United States Patent
Jierry et al.

(10) Patent No.: US 11,879,038 B2
(45) Date of Patent: Jan. 23, 2024

(54) SUPRAMOLECULAR GEL SUPPORTED ON OPEN-CELL POLYMER FOAM

(71) Applicants: UNIVERSITÉ DE STRASBOURG, Strasbourg (FR); CENTRE NATIONAL DE LA RECHERCHE SCIENTIFIQUE, Paris (FR); INSTITUT NATIONAL DE LA SANTE ET DE LA RECHERCHE MEDICALE (INSERM), Paris (FR)

(72) Inventors: Loïc Jierry, Strasbourg (FR); Christophe Serra, Souffelweyersheim (FR); Pierre Schaaf, Molsheim (FR); Jennifer Rodon Fores, Ozoir la Ferriere (FR); Fouzia Boulmedais, Strasbourg (FR)

(73) Assignees: UNIVERSITE DE STRASBOURG, Strasbourg (FR); CENTRE NATIONAL DE LA RECHERCHE SCIENTIFIQUE (CNRS), Paris (FR); INSTITUT NATIONAL DE LA SANTE ET DE LA RECHERCHE MEDICALE, Paris (FR)

( * ) Notice: Subject to any disclaimer, the term of this patent is extended or adjusted under 35 U.S.C. 154(b) by 71 days.

(21) Appl. No.: 17/637,722

(22) PCT Filed: Sep. 9, 2020

(86) PCT No.: PCT/EP2020/075184
§ 371 (c)(1),
(2) Date: Feb. 23, 2022

(87) PCT Pub. No.: WO2021/048199
PCT Pub. Date: Mar. 18, 2021

(65) Prior Publication Data
US 2022/0315710 A1 Oct. 6, 2022

(30) Foreign Application Priority Data

Sep. 9, 2019 (EP) .................................. 19306077

(51) Int. Cl.
*C08J 3/075* (2006.01)
*C08G 83/00* (2006.01)
*C08J 9/40* (2006.01)

(52) U.S. Cl.
CPC ............ *C08G 83/008* (2013.01); *C08J 3/075* (2013.01); *C08J 9/405* (2013.01); *C08J 2205/05* (2013.01);
(Continued)

(58) Field of Classification Search
CPC .... C08J 2489/00; C08J 2205/05; C08J 3/075; C08G 83/008; C12N 11/098; C12N 11/04; C12N 11/16; C12N 11/00; C12P 21/00
See application file for complete search history.

(56) References Cited

U.S. PATENT DOCUMENTS

2007/0224273 A1    9/2007  Xu et al.

FOREIGN PATENT DOCUMENTS

| CN | 109667835 A | 4/2019 |
| WO | 2011063475 A1 | 6/2011 |

(Continued)

OTHER PUBLICATIONS

Li, X. et al. "Short Laminin Peptide for Improved Neural Stem Cell Growth" Stem Cells Translationalmedicine 2014;3:662-670. (Year: 2014).*

(Continued)

*Primary Examiner* — K. Boyle
*Assistant Examiner* — Christina H. W. Rosebach
(74) *Attorney, Agent, or Firm* — WC&F IP

(57) ABSTRACT

The present invention relates to a polymer foam, said polymer foam comprising pores forming an open-cell poly-
(Continued)

mer foam, said polymer foam comprising a supramolecular gel inside pores, and said polymer foam comprising at least one enzyme. The present invention relates to a supramolecular gel; its preparation and its applications, notably in chemical synthesis and kinetic resolution, in particular of organic compounds. The present invention also relates to flow chemistry.

14 Claims, 3 Drawing Sheets

(52) U.S. Cl.
CPC ........ *C08J 2361/28* (2013.01); *C08J 2489/00* (2013.01)

(56) References Cited

FOREIGN PATENT DOCUMENTS

WO   WO-2011063475 A1 *   6/2011   ............ C07K 5/0808
WO   2017106937 A1   6/2017

OTHER PUBLICATIONS

Aumailley, M.The laminin family. Cell Adhesion & Migration 7:1, 48-55. (Year: 2012).*
Catalysis; Catalyst. Hawley's Condensed Chemical Dictionary, Sixteenth Edition. By: Michael D. Larranaga et al. (Year: 2016).*
Zollinger, A.J. et al. Fibronectin, the extracellular glue. Matrix Biol. (2017) 60-61, 27-37 (Year: 2017).*
Amirrah, I.N. et al. "A Comprehensive Review on Collagen Type I Development of Biomaterials for Tissue Engineering: From Biosynthesis to Bioscaffold." Biomedicines 2022, 10, 2307 (Year: 2022).*
Rodon Flores, J. et al. "Supported Catalytically Active Supramolecular Hydrogels for Continuous Flow Chemistry". Angew. Chem. Int. Ed. 2019, 58, 18817-18822 (Year: 2019).*
Guler, M.O. et al. "A Self-Assembled Nanofiber Catalyst for Ester Hydrolysis". J. Am. Chem. Soc. 2007, 129, 12082-12083. (Year: 2007).*
Maeda, Y. et al. "Molecular Self-Assembly Strategy for Generating Catalytic Hybrid Polypeptides" PLoS ONE 11(4): e0153700 (Year: 2016).*
Translation of CN 104736246 by Pontlevoy et al. (Year: 2015).*
Bhattacharyya, T. et al., "Supramolecular Hydrogel Inspired from DNA Structures Mimics Peroxidase Activity", ACS Biomaterials Science and Engineering vol. 3, 2017.
Hickling, C. et al., "Nanofibrillar Peptide Hydrogels for the Immobilization of Biocatalysts for Chemical Transformations", Macromolecular Rapid Communications vol. 35, 2014.
Raymond, D. et al., "Multicomponent Peptide Assemblies", Chem Soc Review vol. 47, 2018.
Shanbhag, B. et al., "Self-Assembled Enzyme Nanoparticles for Carbon Dioxide Capture", Nano Letters vol. 16, 2016.
Weingarten, A. et al., "Self-assembling hydrogel scaffolds for photocatalytic hydrogen production", Nature Chemistry vol. 6, 2014.
Vigier-Carriere, C. et al., "Surface-Assisted Self-Assembly Strategies Leading to Supramolecular Hydrogels", Angewantde Chemie International Edition, 2018.
Zhang, J. et al., "Using Phosphatases to Generate Self-Assembled Nanostructures and their Applications", Antioxidants and Redox Signaling, vol. 20 No. 14, 2014.

* cited by examiner

SUPRAMOLECULAR GEL SUPPORTED ON OPEN-CELL POLYMER FOAM

The present invention relates to supramolecular gel grafted on an open-cell polymer foam.

In particular, a catalytic supramolecular gel has applications in chemical synthesis and kinetic resolution, in particular of organic compounds.

The present invention also relates to flow chemistry.

TECHNOLOGICAL BACKGROUND

Recently a new class of peptides self-assemblies able to both underpin a gel displaying a catalytic activity. In 2009, Pr. Rein V. ULIJN and coworkers have shown the spatial localization of peptides self-assembly on surface through the immobilization of an enzyme [Nat. Nanotech. 4, 19-24 (2009)]: non self-assembling peptides (precursors) can be enzymatically transformed into self-assembling ones (gelators) leading to the growth of nanostructures exclusively from the surface. In parallel, the Institut Charles Sadron has demonstrated the possibility to control micrometric supramolecular gels formation from any kind of planar substrate based on enzymatically-active multilayer films using various peptides and enzymes [Angew. Chem., Int. Ed. 54, 10198-10201 (2015); Angew. Chem., Int. Ed. 56, 15984-15988 (2017); Langmuir 33, 8267-8276 (2017); Angew. Chem., Int. Ed. 57, 1448-1456 (2018); Chem. Sci. (2019) DOI: 10.1039/c9sc00312].

However, the present inventor considers that technological applications of these materials are facing the problem of the inherent mechanical fragility of supramolecular gel prepared from low molecular weight gelators. These gel have no clear industrial application up to day because of this fragility. In particular, these gel cannot be used in flow chemistry.

AIMS OF THE INVENTION

The present invention aims to solve the above-described technical problems.

In particular, the present invention aims to solve the technical problem of providing a material comprising a supramolecular gel for laboratory or industrial applications.

In particular, the present invention aims to solve the technical problem of providing a supramolecular gel having a catalytic activity for chemical reaction.

Another aim of the invention is to solve the technical problem of providing a material comprising a supramolecular gel having a catalytic activity, and said material having sufficient mechanical properties for example to be used in a flow reactor.

DETAILED DESCRIPTION OF THE INVENTION

The present invention relates to a polymer foam, said polymer foam comprising pores forming an open-cell polymer foam, said polymer foam comprising a supramolecular gel inside pores, and said polymer foam comprising at least one enzyme.

In one embodiment, said supramolecular gel comprises nanofibers anchored on the surface of pores of said polymer foam.

Accordingly, there is a non-covalent link between the gel and the polymer foam.

Typically, nanofibers orientated from the bottom to the top generate self-assembling derivatives in the presence of an adequate enzyme.

In one embodiment, said gel forms an entanglement of long fibers (several micrometers) observable by transmission electron microscopy (TEM).

Typically, said supramolecular gel is a supramolecular hydrogel.

In one embodiment, said supramolecular gel comprises auto-assembled molecules called gelators (or hydrogelators in case of hydrogel) obtained by enzymatic modification.

Typically, said gelator is obtained by enzymatic reaction of a molecule, called precursor, comprising a part modified by the enzyme used in the polymer foam of the present invention and a part that is not modified by said enzyme. Typically, the gelators presents a lower water-solubility than the precursor.

In one embodiment, said precursor has both a hydrophobic part (aromatic/aliphatic residues or chemical groups) and a hydrophilic part (polar residues or chemical groups) in its sequence/chemical structure.

In one embodiment, said precursor is an amphiphilic peptide.

In one embodiment, the enzyme modifies the precursor by cleaving a hydrophilic part of the precursor, thereby providing a gelator having lower water-solubility than the precursor.

In one embodiment, said supramolecular gel has at least one catalytic activity.

Advantageously, said supramolecular gel exhibits catalytic activity. It was surprising that the supramolecular gel kept an acceptable, even good, catalytic activity inside a polymer foam.

Also surprisingly, a supramolecular gel according to the present invention exhibit better enzymatic activity than the enzyme. This was typically the case for a supramolecular gel according to the present invention having an esterase-like activity.

Advantageously, in one embodiment, said supramolecular gel comprises peptides.

Advantageously, in one embodiment, said supramolecular gel comprises peptides in water and forms a peptide-based hydrogel.

In one embodiment, nanofibers comprising peptides have a helical shape, typically of antiparallel β-sheet association between the peptides. In one embodiment, said nanofibers have a chiral twisted ribbon shape In one embodiment, said supramolecular gel comprises a polyelectrolyte multilayer comprising the combination of a polycationic compound and a polyanionic compound forming bilayers, said polyelectrolyte multilayer being in between the substrate and the layer of said enzyme.

In one embodiment, said supramolecular gelcatalytic activity is an esterase-like activity, or catalyzes a reaction selected from the group consisting of Aldolization, Mannich Reaction, Michael addition, hydrolysis of glycosidic bonds, Diels-Alder reaction in the presence of Cu(II) ions, oxidation of benzyl alcohol in the presence of Pd(II) ions, triazole formation by cycloaddition in the presence of Cu(I) ions, peroxidase activity in the presence of Fe(II) ions and a heme nucleus, $CO_2$ to carbonate conversion in the presence of Zn(II) ions and any combination thereof.

For example Wang, H., Li, D. & Wang, L. Molecular Gels with Esterase-Like Activity. Chin. J. Chem. 31, 494-500 (2013) describe such esterase-like catalytically-active supramolecular gel, which is incorporated by reference. This peptide is not soluble in water at room temperature but when a suspension of this peptide is heated close to 100° C. and then cooled slowly, an esterase-like gel is obtained, reactive towards the activated ester 4-nitrophenyl acetate (PNA).

In one embodiment, said peptide is a heptapeptide, preferably having tyrosine residues (Y) in positions 4 and 7.

In one embodiment, said peptide presents a protecting group of the terminal amine, for example a Fmoc group in N-terminal position.

In one embodiment, said peptide is Fmoc-GFFYGHY of following formula:

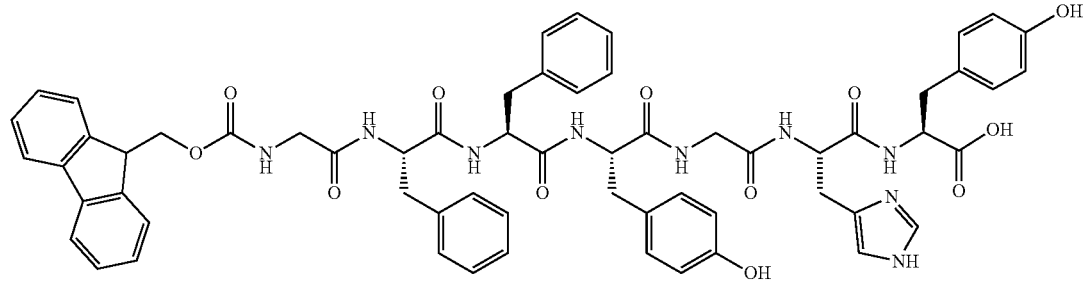

Fmoc-GFFYGHY

Preferably, said enzyme is adsorbed in the pores of said polymer foam.

Advantageously, said supramolecular gel exhibits catalytic activity. It was surprising that the enzyme kept an acceptable, even good, catalytic activity inside a polymer foam.

In one embodiment, said supramolecular gel is an enzyme-assisted self-assembly gel.

In one embodiment, said supramolecular gel is an enzyme-assisted self-assembly peptide-based gel.

Typically the enzyme is said enzyme is selected from the group consisting of esterase, phosphatase, alkaline phosphatase, β-lactamase, matrix metalloproteinase, matrix metalloproteinase-9 (MMP-9), chymotrypsin, thrombin, galactosidase, lipase, microbial transglutaminase (MTGase), thermolysin, glucose oxidase, peroxidase, tyrosinase, and any combination thereofgelgel.

In one embodiment, said enzyme is an alkaline phosphatase.

Preferably said, enzyme is adsorbed in said supramolecular gel.

Accordingly, in one embodiment, said polymer comprises a layer of the polymer material forming a substrate, a layer of said supramolecular gel on said substrate, said enzyme being adsorbed in said supramolecular gel.

Typically, said polymer foam of the present invention comprises an open-cell scaffolding of foam, the scaffolding comprising a multiplicity of interconnected, three-dimensionally branched channels.

Typically, a foam is a dispersion in which a gas (typically a large proportion of gas by volume) in the form of gas bubbles, is dispersed in a liquid, solid or gel. The diameter of the bubbles is usually larger than 1 μm, but the thickness of the lamellae between the bubbles is often in the usual colloidal size range. The term froth has been used interchangeably with foam. In particular cases froth may be distinguished from foam by the fact that the former is stabilized by solid particles (as in froth flotation q.v.) and the latter by soluble substances (Source: PAC, 1972, 31, 577 (*Manual of Symbols and Terminology for Physicochemical Quantities and Units, Appendix II: Definitions, Terminology and Symbols in Colloid and Surface Chemistry*) on page 606).

According to the present invention, said supramolecular gel is embedded into the pore structure of said polymer foam.

Advantageously, according to the invention, the polymer foam provides mechanical robustness to said supramolecular gel.

In one embodiment, said polymer foam is selted from the group consisting of Ethylene-vinyl acetate (EVA) foam, copolymers of ethylene and vinyl acetate; also referred to as polyethylene-vinyl acetate (PEVA), Low-density polyethylene (LDPE) foam, first grade of polyethylene (PE), Nitrile rubber (NBR) foam, copolymers of acrylonitrile (ACN) and butadiene, Polychloroprene foam, Neoprene, Polyimide foam, Polypropylene (PP) foam, expanded polypropylene (EPP) and polypropylene paper (PPP), Polystyrene (PS) foam, including expanded polystyrene (EPS), extruded polystyrene foam (XPS), polystyrene paper (PSP), Styrofoam, extruded polystyrene foam (XPS) and sometimes expanded polystyrene (EPS), Polyurethane (PU) foam, LRPu low-resilience polyurethane, Memory foam, Sorbothane, Polyethylene foam, Polyvinyl chloride (PVC) foam, Silicone foam, Microcellular foam, formaldehyde-melamine-sodium bisulfite copolymer (melamine foam).

In one embodiment, said polymer foam is a melamine-formaldehyde resin foam, typically a formaldehyde-melamine-sodium bisulfite copolymer (melamine foam). A suitable melamine-formaldehyde resin foam raw material is commercially available under the trade name Basotect® from BASF.

In one embodiment, said polymer foam is an open cell melamine foam

In one embodiment, said polymer foam has diameter cells of roughly from 50 to 500 μm. In one embodiment, said open cell polymer foam has a porosity of about 45 PPI (pores per inch). Advantageously, said open polymer cell foam has a porosity of less than 45 PPI. More advantageously, said open polymer cell foam has cells having a diameter of 200 μm or less.

Typically, open cell polymer foams are in the form of structures composed of interconnected cells and randomly and/or orderly distributed throughout the structure of the elastomeric material. As a first approximation, these cellular foams have a regular pentagonal dodecahedron type geometrical shape.

In one embodiment, the hydrodynamic porosity (i.e. the ratio of the volume directly accessible by a liquid (which would pass through the foam from side to side) with respect to the total volume of the open cell foam) is of 0.5 to 0.99, especially 0.7 to 0.99, more preferably 0.8 to 0.98.

In one embodiment, the density of the foam is of 1 to 50 kg/m$^3$, especially 1 to 20 kg/m$^3$ and more preferably 7 to 15 kg/m$^3$.

In one embodiment, the Young modulus of the open cell polymer foam is 10 to 1000 kPa, especially 20 to 200 kPa and more preferably 40 to 100 kPa. Typically Young modulus is not significantly modified when comprising a gel according to the present invention.

The present invention also relates to a method for preparing a polymer foam according to the present invention, said method comprising:
  (a) providing a polymer foam comprising pores forming an open-cell polymer foam,
  (b) providing an enzyme inside said pores of said polymer foam, and
  (c) providing a molecule forming a supramolecular gel inside pores of said polymer foam.

Typically, when said enzyme is added to a solution, typically an aqueous solution, of peptides, a gel, typically a hydrogel, forms almost instantaneously.

Typically, said enzyme is selected among enzymes enzymatically active on said molecule (the molecule (precursor) being a substrate for the enzyme) thereby forming a supramolecular gel. Typically, the enzyme modifies a precursor in a gelator which provides the supramolecular gel. As examples, an alkaline phosphatase is added to a solution of phosphate-containing peptide, an esterase is added to a solution of peptides having at least one ester bond, or an oxidase is added to a solution of peptides having at least one oxidable bond, to form said supramolecular gel.

In one embodiment, said phosphate-containing peptide is Fmoc-GFFpYGHpY:

polymer foam. Finally, the peptide (typically a peptide solution) is let in contact with the modified surface to provide a supramolecular hydrogel inside pores by enzymatic activity of said enzyme. Typically, the method comprises intermediate rinsing step. All steps are typically performed at room temperature.

In one embodiment, wherein step (c) comprises providing a peptide as molecule forming said supramolecular gel and growing supramolecular gel inside pores by enzymatic activity of said enzyme.

Typically, the precursor is solubilized in an aqueous solution and the supramolecular gel is formed in an aqueous medium thereby forming a hydrogel.

An aqueous medium is typically water. In one embodiment, said aqueous medium is a mixture of water and another solvent of the precursor, for example an alcohol.

In one embodiment, for example depending on the desired application, said hydrogel may be put into contact with an organic solvent by replacing the aqueous medium by an organic medium, thereby forming an organogel.

The present invention also relates to a flow reactor comprising a polymer foam according to the present invention or obtainable by a method as defined in the present invention.

Advantageously, the polymer foam of the present invention is stable.

It was though prior to the invention that delamination of the supramolecular gel which is a physical gel resulting from the self-assembly of molecules. More precisely, a gradual delamination of the supramolecular gel through the shear stress induced by the flow in a chemical flow reactor was thought to be the most credible issue. Surprisingly, the inventors discovered that polymer foam of the present invention was stable with respect to flow and over time. Even more surprising, the inventors discovered that a poly-

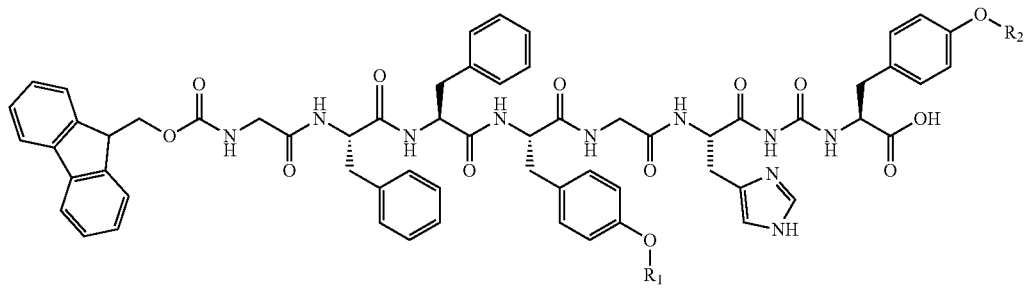

Fmoc-GFFpYGHpY ($R_1 = R_2 = -PO_3^{2-}$)

In one embodiment, step (b) comprises coating said pores with a polyelectrolyte multilayer comprising the combination of a polycationic compound and a polyanionic compound forming bilayers prior to providing said enzyme and then coating said polyelectrolyte multilayer with said enzyme.

Typically, the gelator is obtained by modifying a precursor by the enzyme activity thereby forming the supramolecular gel.

in one embodiment, a first layer of polyelectrolyte (for example Poly(ethylene imine) (PEI)) is deposited inside pores of the polymer foam, forming a precursor layer; then a polyelectrolyte multilayer is built up by alternately exposing the surface to oppositely charged polyelectrolyte solutions. Then, the enzyme is put in contact with the resulting mer foam supporting the present invention exhibited an enzyme catalytic activity. Advantageously, no serious loss of catalytic activity was observed.

Advantageously, a polymer foam of the present invention has at least one catalytic activity. Advantageously, the supramolecular gel has a catalytic activity, called enzymatic-like gel activity. It is said "like" because the gel activity is not provided by an enzyme but by the supramolecular gel.

Advantageously, in an embodiment, a polymer foam of the present invention provides an esterase activity, called esterase-like gel activity.

Advantageously, a polymer foam of the present invention exhibits both a catalytic activity provided by said supramolecular gel and an enzymatic activity provided by an enzyme embedded in the supramolecular gel, typically the enzyme assisting the supramolecular gel formation.

Advantageously, a polymer foam of the present invention exhibits both a catalytic activity provided by a peptides self-assembly in said supramolecular gel and an enzymatic activity provided by an enzyme embedded in the supramolecular gel.

In one embodiment, said polymer foam comprises catalytic particles, preferably catalytic nanoparticles.

In one embodiment, a polymer foam of the present invention comprises at least a phosphatase enzyme providing a phosphatase enzymatic activity.

In one embodiment, said polymer foam has multiple catalytic activity. Advantageously, the catalytic activities of the foam of the present invention is provided by the supramolecular gel and the enzymatic activity of the enzyme present in the foam.

In one embodiment, said polymer foam comprises multiple enzymes having each a different catalytic activity.

In one embodiment, said polymer foam comprises at least one enzyme and at least one catalytic particle, preferably catalytic nanoparticle.

In one embodiment, said polymer foam has an esterase-like gel activity and a phosphatase enzymatic activity.

Continuous flow chemistry appears particularly well adapted for a polymer foam of the present invention since the flow through the catalytic gel compensates the low diffusion rate of substrates under static conditions (decreasing thus the reaction time) and provides also an easy separation way between products and the catalytic phase.

Advantageously, a polymer foam of the present invention allows performing chemical reactions and/or kinetic resolution in an aqueous phase.

The present invention also relates to a method for chemical synthesis comprising putting one or more chemical reactants in contact with a polymer foam according to the present invention or obtainable by a method as defined according to the present invention, converting said chemical reactant into one or more chemical products by catalytic reaction by said polymer foam.

The present invention also relates to a method for chemical synthesis comprising putting one or more chemical reactants in contact with a polymer foam according to the present invention or obtainable by a method as defined according to the present invention, converting said chemical reactant into one or more chemical products by catalytic reaction by said polymer foam.

In a specific embodiment, a polymer foam of the present invention catalyzes a reaction selected from the group consisting of Aldolization, Mannich Reaction, Michael addition, hydrolysis of glycosidic bonds, Diels-Alder reaction.

In a specific embodiment, in the presence of Cu(II) ions, oxidation of benzyl alcohol in the presence of Pd(II) ions, triazole formation by cycloaddition in the presence of Cu(I) ions, peroxidase activity in the presence of Fe(II) ions and a heme nucleus, CO2 to carbonate conversion in the presence of Zn(II) ions and any combination thereof.

In a specific embodiment, a polymer foam of the present invention having an esterase enzyme provides efficient esterase-like gel active towards activated esters but also towards a large panel of inactivated substrates such as methyl, primary, secondary and tertiary ester classes.

In a specific embodiment, a polymer foam of the present invention having an esterase enzyme provides kinetic resolution capacity allowing to isolate quantitative amount of enantiopure carboxylic acids from racemic or enantio-enriched inactivated esters.

In a specific embodiment, methyl esters 1, 9, primary ester 3 and secondary ester 5 are quasi quantitatively converted in their corresponding carboxylic acids 2, 10, 4 and 7 respectively.

In a specific embodiment, ester 4-nitrophenyl acetate (PNA) is converted into para-nitrophenol.

In one embodiment, the present invention relates to a method for preparing carboxylic acids. In one embodiment, the present invention relates to a method for hydrolyzing esters.

Advantageously, chemical reactive groups such as phenol, carboxylic acid or amine, do not affect the catalytic efficiency of the catalytic material of the invention.

In a specific embodiment, a complex structure, such as 3, self-assembles when its ester moiety is chemically cleaved giving thus rise to a second self-assembled architecture growing within the supramolecular gel having an esterase-like gel active towards activated esters.

Advantageously, a polymer foam of the present invention exhibits kinetic resolution.

Advantageously, a polymer foam of the present invention exhibits kinetic resolution of racemic esters.

In a specific embodiment, a polymer foam of the present invention exhibits kinetic resolution of inactivated esters, for example with a strong discrimination between the L and D amino-acid tertiobutyl esters 6.

In a specific embodiment, a polymer foam of the present invention exhibits kinetic resolution of oxirane of 4-methoxycinnamic methyl ester. The (R,R) enantiomer is hydrolyzed faster than the (S,S) one: this compound is a key intermediate in the industrial preparation of the Diltiazem, a drug used to treat high blood pressure, angina and certain heart arrhythmias.

Advantageously, a polymer foam of the present invention provides an easy separation way between products and the catalytic phase.

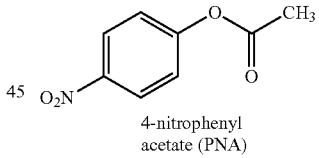

4-nitrophenyl acetate (PNA)

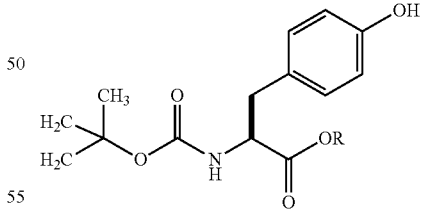

1: R = Me
2: R = H

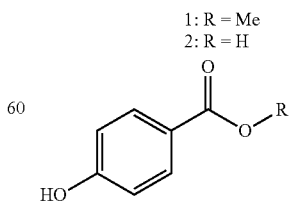

5: R = CH(CH$_3$)$_2$
7: R = H

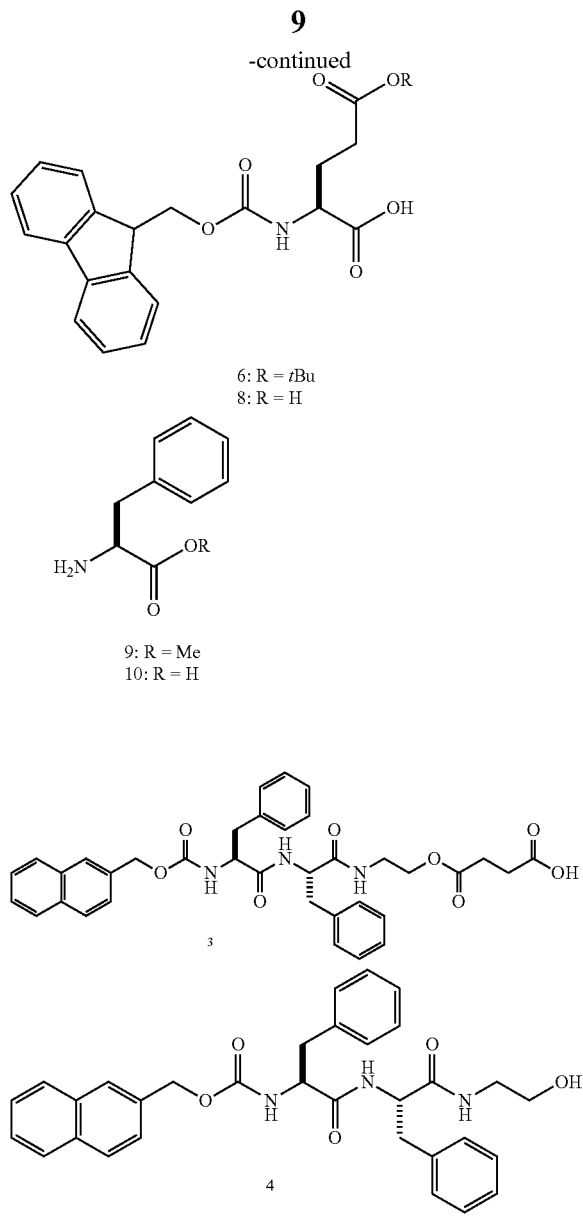

EXAMPLES

All chemicals used in this work are gathered in the following table. They were all used as received, without further purifications.

| Name, acronym (abbreviation) | MW (g.mol$^{-1}$) | Supplier | CAS number |
| --- | --- | --- | --- |
| Bovine serum albumin (BSA) | 66 000 | Sigma-Aldrich | 9048-46-8 |
| Alkaline Phosphatase from bovine intestinal mucosa (AP) | 170 000 | Sigma-Aldrich | 9001-78-9 |
| Poly(ethylene imine) (PEI) | 750 000 | Alfa Aesar | 9002-98-6 |
| Poly(styrene sulfonate) (PSS) | 70 000 | Sigma-Aldrich | 25704-18-1 |
| Deuterated Water (D$_2$O) | 20.03 | Sigma-Aldrich | 7789-20-0 |
| Dimethylformamide (DMF) | 73.09 | Acros Organics | 68-12-2 |
| Dichloromethane (DCM) | 84.93 | Acros Organics | 75-09-2 |
| Trifluoroacetic acid (TFA) | 114.02 | Alfa Aesar | 76-05-1 |
| Deuterated DMSO (DMSO-d$_6$) | 84.17 | SDS | 2206-27-1 |
| N-Ethyldiisopropylamine (DIEA) | 129.25 | Alfa Aesar | 7087-68-5 |
| Fmoc-L-phenylalanine (Fmoc-F-OH) | 387.43 | Iris biotech | 35661-40-6 |
| Fmoc-L-Tyrosine Phosphate (Fmoc-Y(PO$_3$H$_2$)-OH | 483.41 | Bachem | 147762-53-6 |
| Fmoc-L-Glycine (Fmoc-G-OH) | 297.31 | Iris biotech | 29022-11-5 |
| Fmoc-trityl-L-Histidine (Fmoc-H(Trt)-OH | 619.71 | Iris biotech | 109425-51-6 |
| Triisopropylsilane (TIPS) | 158.36 | Sigma-Aldrich | 6485-79-6 |
| Resin 2-chlorotrityl chloride (2-CTC) | — | Sigma-Aldrich | 42074-68-0 |
| 1-Hydroxybenzotriazole hydrate (HOBt) | 135.12 | Sigma-Aldrich | 123333-53-9 |
| N,N,N',N'-Tetramethyl-o-(IH-benzotriazol-1-yl)uranium hexafluorophosphate (HBTU) | 379.24 | Alfa Aesar | 94790-37-1 |
| Diethyl ether | 74.12 | Acros Organics | 60-29-7 |
| Polymer Foam (melamine) BASOTCT V3012 white | / | FoamPartner | / |
| L-Phenylalanine methyl ester hydrochloride | 215.68 | Sigma-Aldrich | 7524-50-7 |
| 4-Nitrophenyl acetate (PNA) | 181.15 | Sigma-Aldrich | 830-03-5 |
| Fmoc-L-glutamic acid 5-tert-butyl ester (Fmoc-L-Glu(OtBu)-OH) | 425.47 | Sigma-Aldrich | 71989-18-9 |
| Fmoc-D-glutamic acid 5-tert-butyl ester (Fmoc-D-Glu(OtBu)-OH) | 425.47 | Sigma-Aldrich | 104091-08-9 |
| Fmoc-L-aspartic acid 4-tert-butyl ester (Fmoc-L-Asp(OtBu)-OH) | 411.25 | Sigma-Aldrich | 71989-14-5 |
| Fmoc-L-Lysine t-butyl ester hydrochloride (Fmoc-L-Lys-OtBu) | 460.98 | Iris Biotech GMBH | 940941-43-5 |
| Fmoc-D-Lysine t-butyl ester hydrochloride (Fmoc-D-Lys-OtBu) | 460.98 | Iris Biotech GMBH | 2250436-42-9 |
| 4-Hydroxybenzoïc acid isopropyl ester (Isopropyl 4-hydroxybenzoate) | 180.20 | Sigma-Aldrich | 4191-73-5 |
| Boc-L-Tyrosine methyl ester (Boc-L-Tyr-OMe) | 295.33 | Sigma-Aldrich | 4326-36-7 |
| Fmoc-L-tyrosine tert-butyl ester (Fmoc-L-Tyr-OtBu) | 237.29 | Sigma-Aldrich | 16874-12-7 |
| D-tyrosine tert-butyl ester (H$_2$N-D-Tyr-OtBu) | 237.29 | Alfa Aesar | 87553-74-0 |
| Fmoc Chloride | 258.70 | Sigma-Aldrich | 28920-43-6 |

Transmission Electronic Microscopy (TEM)

Figure 1:
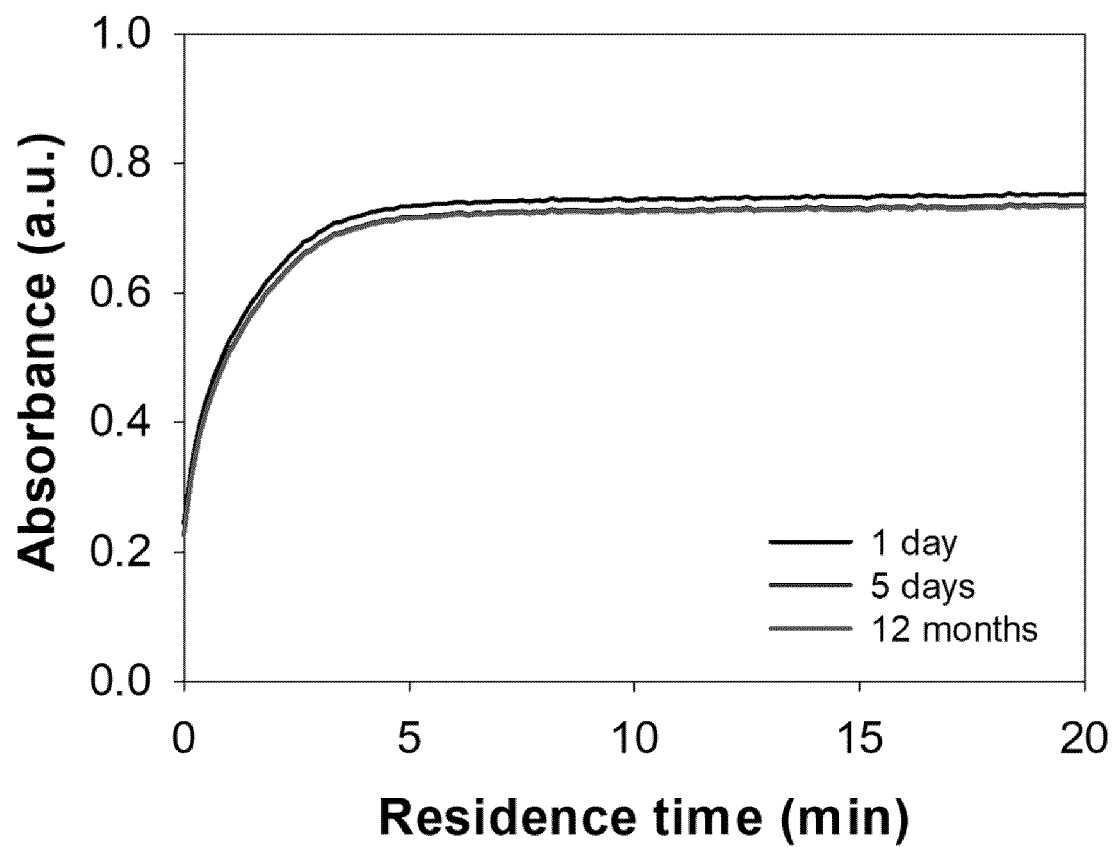
FIG. 1 represents a monitoring of para-nitrophenol production from PNP hydrolysis by HPLC as illustrated in example 11. Absorbance (405 nm) evolution over residence time is measured for three runs: one day (black line), five days (red line) and twelve months (green line) after the preparation of the supported supramolecular hydrogel (black).

The TEM images were performed with sample prepared in liquid (diluted solutions (1 mg/mL of Fmoc-GFFpYGHpY and Fmoc-GFFYGHY) or gels (10 mg/mL of Fmoc-GFFpYGHpY or Fmoc-GFFYGHY (prepared as described in section 2 just above))). All the samples were freshly prepared before TEM measurements. To make the observations 20 µL of the sample is dropped off on a shelf. Then, the sample is observed by a TEM Tecnai G2 machine in negative staining. To make the observations, 5 µL of the different gels are deposited onto a freshly glow discharged carbon-covered grid (400 mesh). The gel is left for 2 minutes and the grid is negatively stained with 5 microliters uranyl acetate (2% in water) for another minute and finally dried using a filter paper. The grids were observed at 200 kV with a Tecnai G2 (FEI) microscope. Images were acquired with a camera Eagle 2k FEI) ss CD camera.

Analytic High-Performance Liquid Chromatography (HPLC)

Analytic High-Performance Liquid chromatography (HPLC) was carried out with a 1100 Series from Agilent technologies.

For characterization of the different peptides and the catalytic assays: the column is a Supelcosil ABZ+Plus with the following dimensions 15 cm×4.6 mm, 3 µm. The eluent used for all analyses was acetonitrile/deionized water in different ratios depending on the experiment. Ratio 80/10 in isocratic conditions, at 1 mL/min for the first catalytic assays but a ratio 50/50 in isocratic conditions, at 1 mL/min for the peptide characterization.

For the racemic discrimination assays: the column is a chiral column is a Cosmosil 3B with the following dimensions 4.6 mm I.D.×250 mm. The eluent used for all analyses was n-hexane/isopropanol in ratio 90/10 in isocratic conditions, at 1 mL/min except for the racemic solution of methyl-3-(4-methoxyphenyl) oxirane-2-carboxylate where the ratio was 97.5/2.5 in isocratic conditions at 1 mL/min. Chromatograms were recorded by the software OpenLab Agilent 1100.

All samples were observed in solution in diluted conditions (ten times under the gelation condition (1 mg/mL of peptides)).

Example 1—Synthesis and Characterization of Fmoc-GFFYGHY, Fmoc-GFFpYGHY, Fmoc-GFFYGHpY and Fmoc-GFFpYGHpY All peptides were prepared using solid support chemistry. The "Fmoc strategy" was used based on 2-CTC resin. The following synthetic pathway is given in the scheme below:

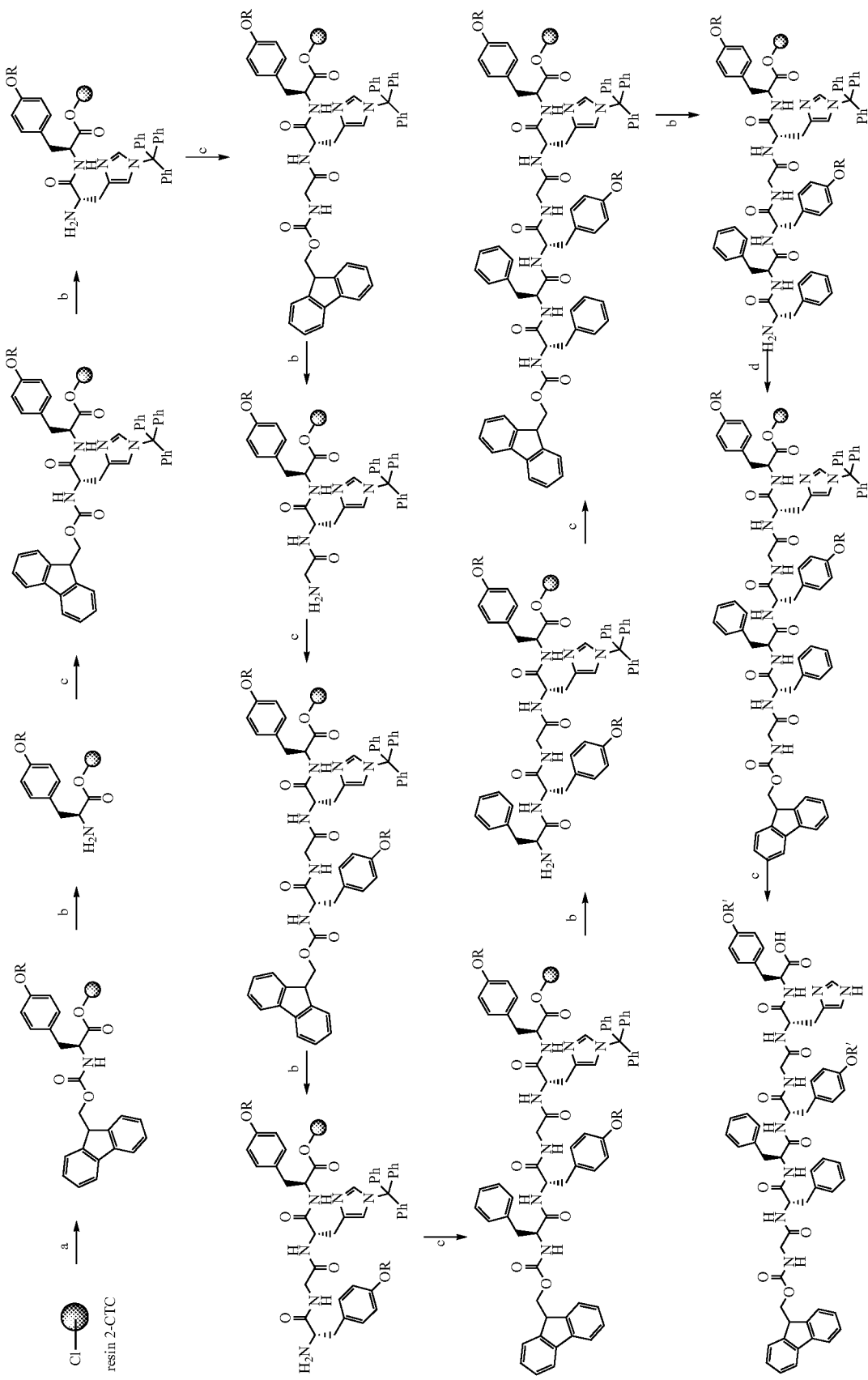

Step a: loading of the resin 2-chlorotrityl chloride (2-CTC, called as "resin" or "r" in the rest of this procedure). Addition of 3 eq/r of Fmoc-Tyr(OR)—OH+6 eq/r of DIEA in 3 mL of DMF for 300 mg of resin. The solution in contact with the resin is stirred at RT for 2 h. Then, the solution is removed and a solution of MeOH is added at RT for 1 h.

Step b: Fmoc group deprotection: 3 mL of a 20% of piperidine in DMF solution is added and stirred at RT for 15 min.

Step c: Coupling step: 3eq/r of Fmoc-amino acid+3 eq/r of HOBt+3 eq/r of HBTU+6 eq/r of DIEA are added in 3 mL of DMF and let in contact with the resin at RT for 30 min.

Step d: Cleavage of the resin and lateral chains deprotection: addition of 3 mL of a solution containing 95% TFA+2.5% $H_2O$+2.5% triisopropylsilane it's stirred at RT for 2 h. Then the solution is filtered. The solvent is then removed. Finally the product is precipitated by using a small amount of cold ether.

Between each step a, b, c and d, a rinsing stage is executed by using 5 times 3 mL of DMF and then a Kaiser test is made to confirm the achievement of the coupling or deprotection steps.

When the amino acid Fmoc-Tyrosine-OH was required in the final sequence, the protection of the phenol group was ensured by a tBu group. When a tyrosine-phosphate is required, the Fmoc-Tyr(OPO3H2)-OH is directly introduced during the synthesis.

Example 2—Preparation of Peptide Solution and Gel Formation

All gels were prepared in PBS buffer (pH 7.4). The PBS buffer is prepared the day of the gel preparation.

PBS Buffer (pH 7.4): one tablet of commercially available PBS (P4417 from Sigma Aldrich) was dissolved in 200 mL of ultrapure water (Milli-Q Plus system, Millipore, Billerica, MA) leading to 0.001 M phosphate buffer, 0.0027 M potassium chloride and 0.137 M sodium chloride. If necessary, the pH of this buffer was adjusted to 7.4 value by addition of few drops of HCl (0.01 M) or NaOH (0.01 M) solution. The pH value was monitored using a pH meter.

General preparation of peptide solution: an adequate amount of peptide was dissolved in PBS to get the suitable concentration (usually 1 and 10 mg/mL). This solution was vortexed 2-5 minutes and sonicated in an ultrasound bath during 1 minute. The resulting peptide solution was thus used for all kinds of analyses described in this ESI. Fmoc-GFFYGHY gel formation were obtained by dissolving Fmoc-GFFYGHY (10 mg/mL) in PBS buffer. This solution was vortexed during 2 minutes and then dipped into an ultrasound bath during 1 minute. The solution was heated at around 100° C. to solubilize the peptide. When the solution cooled down the gel formed. Fmoc-GFFpYGHpY gel formation were obtained by dissolving Fmoc-GFFpYGHpY (10 mg/mL) in PBS buffer. This solution was vortexed 2 minutes and then dipped into an ultrasound bath during 1 minute. 1 mg/mL of commercial AP (P7640 from Sigma Aldrich) was added (ratio AP/peptide (1/10). The resulting mixture was vortexed 10 seconds. The resulting gel was obtained after 5 minutes Upside-down vial tests with peptides for the gelation assays. Gels were obtained from Fmoc-GFFYGHY by heating and cooling and from Fmoc-GFFpYGHpY using AP, as described above. No gels were obtained from mono-phosphorylated peptides Fmoc-GFFYGHpY or Fmoc-GFFpYGHY using heating/cooling, AP or by decreasing the pH.

Example 3—Multilayer Film Preparation and Localized Gel Formation at the Liquid-Solid Interface All polyelectrolytes (1 mg/mL), proteins (AP 1 mg/mL and BSA 1 mg/mL), and peptides or amino acid (1 mg/mL) were prepared in PBS buffer freshly prepared as described in example 2. Different solid substrates were used depending on the characterization technique investigated: gold coated quartz crystal for QCM-D monitoring, ZnSe crystal for ATR-FTIR experiments, Glass slide and Si Wafer for Cryo-SEM analyses, glass slide for fluorescence emission assays (using a multiplate reader (FLX-Xenius®, SAFAS, Monaco)) and melamine foam (from Foam Partner industry) for activity assays in the continuous flow reactor experiments. The growth of the supramolecular gel from the chosen substrate was done as following: after the deposition of a PEI (1 mg/mL) precursor layer on the chosen surface by dipping (for 10 minutes in the PEI solution), the multilayer film was built up by alternately exposing the surface to PSS (1 mg/mL in PBS buffer) and PEI (1 mg/mL in PBS buffer) solutions for 10 minutes with an intermediate rinsing step with PBS buffer during 5 minutes. AP (1 mg/mL) or BSA (1 mg/mL), all prepared in PBS, were put in contact with the substrate during 20 minutes followed by 5 minutes of rinsing step with PBS buffer. Finally, the peptide Fmoc-GFFpYGHpY solution (1 mg/mL in PBS buffer) was let in contact with the modified surface overnight. The volume of each solution brought in contact with the substrate was 1 mL except for the QCM-D experiment where it was 700 µL. All steps were done at RT.

Example 4—Esterase-Like Activity Assays

Esters Samples preparation: Different concentrations of esters were used: 0.275 mM, 0.55 mM, 1.35 mM, 2.2 mM, 2.76 mM, 2.76 mM, 8.2 mM, 10 mM, 22 mM, 28 mM and 41 mM. Esters were solubilized in ultrapure water. 20 µL of the solution is diluted in 300 µL of isopropanol and then 50 µL of the new solution is added in 450 µL of the eluent ratio of n-hexane and isopropanol.

Solutions were prepared in the eluent ratio of ACN/water and n-hexane/isopropanol. All solutions were filtrated with a PTFE 0.2 µm filter before each injection.

Example 4.1. With Para-Nitrophenyl Acetate (PNA)

Microplate reader UV spectroscopy (FLX-Xenius®, SAFAS, Monaco) using SP2000V7 software was the main device entailed in esterase-like activity measurement toward PNA. The activity of the Fmoc-GFFYGHY gel (formed by the dephosphorylation of Fmoc-GFFpYGHpY in presence of AP) was measured on three kinds of samples: first one in solution with a self-standing gel; second by generating the gel on a surface on a glass slide coated beforehand with the following multilayer PEI/(PSS/PEI)2/AP (protocol described in example 3) and finally by coating on a polymer open-cell foam with the multilayer PEI/(PSS/PEI)2/AP. Concentration (1 mM) and volume (1 mL) ensure a large excess of p-NPA to monitor the esterase like activity through the absorbance measurements at 405 nm (corresponding to the para-nitrophenol maximum absorption).

Example 4.2. With One of the Three Classes of Non-Activated Esters

All experiments were followed by HPLC. Esters (1 mM) were dissolved in a freshly prepared PBS buffer at pH 7.4. Then, 50 μof this ester solution were dropped off on the catalytic gel (see figure below). The gel is formed in the bulk in a 4 mL glass vial, from a PBS buffer solution thanks to the dephosphorylation of Fmoc-GFFpYGHpY (10 mg/mL) in the presence of AP (1 mg/mL). 200 μL of this catalytically-active supramolecular gel (CASH) is formed and 50 μL of different ester solutions (1 mM) are brought in contact with it. The solution of ester diffuses within the CASH and the monitoring of the ester hydrolysis is monitored as following: (i) the CASH containing the ester solution is vortexed and mixed with 1 mL of deionized water, (ii) 10 μL of this solution is mixed with 1 mL of deionized water and (iii) and 5 μis analyzed by HPLC.

Example 5—Esterase-Like Activity and Kinetic Resolution of the Supported CASH in a Continuous Flow Reactor Enzymatically active multilayer film deposition on foam surface: all polyelectrolytes (1 mg/mL), enzyme (AP 1 mg/mL), and Fmoc-GFFpYGHpY (1 mg/mL) were freshly prepared in PBS buffer as described in example 3 above. After the first deposition of a PEI (1 mg/mL) precursor layer on the foam surface by dipping, the multilayer film was built up by alternately exposing the foam in PSS (1 mg/mL in PBS buffer) and PEI (1 mg/mL in PBS buffer) solutions for 10 minutes with an intermediate rinsing step with PBS buffer during 5 minutes. AP (1 mg/mL) solution was prepared in PBS, put in contact during 20 minutes followed by 5 minutes of rinsing step with PBS buffer. Finally, the Fmoc-GFFpYGHpY solution (1 mg/mL in PBS buffer) was brought in contact with the modified foam installed already within the reactor (column) through a continuous flow (in a closed circuit) of 0.5 mL/min during 12 h.

Ester solution: according to the desired ester concentration, the desired amount of ester was dissolved in 20 mL of deionized water before flow catalysis.

Protocol for flow catalysis: the solution of substrate (ester) was introduced in the reactor at 1.5 mL/min flow in a closed circuit. In open circuit (continuous flow conditions) the flow was adapted (decreased) to the desired residence time. For all substrates (except in case of PNA) the conversion in the corresponding carboxylic acid and the enantiomeric excess were followed by HPLC using an adequate column.

Washing step of the flow reactor (column): a solution of 10 mL of deionized water was passed through the flow reactor at 0.5 mL/min flow in an open circuit in the case of PNA and at 1.5 mL/min for all others esters. The resulting solution was checked by HPLC or by UV (in the case of PNA) to be sure that all residual ester or acid have been removed from the reactor. This absence of gelator in the resulting solution supports that the gel is not delaminated.

Quantitative production and isolation of chemically pure and enantiopure Fmoc-L-Glu(OH)—OH: when the conversion of Fmoc-L-Glu(OtBu)—OH in Fmoc-L-Glu(OH)—OH reached 80% after 30 min of time residence (monitored by HPLC/before the hydrolysis of Fmoc-D-Glu(OtBu)—OH in Fmoc-D-Glu(OH)—OH), the reaction is stopped: all the reaction medium is removed from the reactor and this latter is washed with deionized water (see paragraph just above). Then, the reaction medium and the washing solution are gathering and basified up to pH 10 using NaHCO$_3$ (0.5 M) solution. This aqueous phase is extracted three times with dichloromethane (equivalent volume as the aqueous phase). The organic phase is dried on magnesium sulfate and the solvent is removed under reduced pressure. The aqueous phase is neutralized using 0.1 HCl and then freeze-dried. The Fmoc-L-Glu(OH)—OH is isolated as a white solid from the aqueous phase and the enantio-enriched mixture of Fmoc-L-Glu(OtBu)—OH and Fmoc-D-Glu(OtBu)—OH is isolated as a colourless oil from the organic phase.

Example 6—Repeatability of the Catalytic Process

The flow reactor has been prepared as described in Example 5. A solution of the model ester substrate, i.e. para-nitrophenylacetate PNA, (1 mM in 20 mL of deionized water) is injected through the catalytic flow reactor using the flow rate value: 1.5 mL/min. The conversion of PNA in the product para-nitrophenol is monitored over time by HPLC analysis. Once the conversion is completed, the flow reactor is washed with deionized water until no traces of residual para-nitrophenol is detected by HPLC analysis (washing step). This allows to get the kinetic profile of run 1. Then, a freshly prepared new solution of PNA (1 mM in 20 mL of deionized water) is injected through the catalytic reactor at 1.5 mL/min of flow rate. The HPLC monitoring of the PNA conversion over time allows to get the run 2 kinetic profile. Then, a third, fourth and fifth catalytic cycle were successively realized using the same catalytic hydrogel supported foam, corresponding to run 3, 4 and 5 respectively. Comparison between the kinetic profiles of run 1, 2, 3, 4 and 5 shows an excellent repeatability of the catalytic process.

Example 7—Robustness of the Catalytic Process Overtime

Five successive runs were performed as described in example 8, transforming PNA in para-nitrophenol. Then, the tubular column containing the catalytic hydrogel supported on the polymer foam is stored at 4° C. One month later, this column is adapted again for continuous flow reaction in conditions described in example 8. A solution of PNA (1 mM in 20 mL of deionized water) is injected through the catalytic flow reactor using the flow rate value: 1.5 mL/min. The conversion of PNA in the product para-nitrophenol is monitored over time by HPLC analysis (run 6). The graph showing the evolution to the para-nitrophenol production over time of run 6 can be overlapped to those corresponding to run 1, 2, 3, 4 and 5.

Example 8— Stability of the Supported Supramolecular Hydrogel

Five successive runs (run 1, 2, 3, 4 and 5) and one additional run one month later (run 6) were realized as described in examples 9 and 10. HPLC monitoring was carried out during all these six runs to detect any leaching of the peptide hydrogelator Fmoc-GFFYGHY during both the catalytic flow processes and the washing steps. In any cases, no traces of the hydrogel-constituting peptide was measured proving no delamination of the peptide self-assembled structure. This observation is in full agreement with the preservation of the catalytic activity over the several runs, highlighting the good stability the supported supramolecular hydrogel in the flow catalytic process.

Example 9—Determination of the Proportion of Peptides Involved in the Catalytic Process The number of peptide Fmoc-GFFYGHY that has been reacted with PNA is estimated from FIG. 3a and is equivalent to 141 µmoles: this is the amount of PNA converted when 22, 28 and 41 mM of PNA is used. We postulate that one PNA has reacted with one histidine. To determine the ratio of peptides Fmoc-GFFYGHY that have reacted with PNA against peptides present in the CASH within the investigated tubular column (15 cm length and 4 mm diameter, see 4b in the manuscript), the supported gel was entirely dissolved using a flow of acetone. After the removal of this organic solvent under reduced pressure, the residue was first analyzed by 1H NMR and HPLC to confirm the solely presence of Fmoc-GFFYGHY, and then weight. A mass of 1.66 mg (1.49 mmoles) was isolated as a white solid. Thus, the ratio r of peptide involved in the catalytic process against the whole number of peptide Fmoc-GFFYGHY engaged in the CASH is: r=1490/141≈111.

Example 10—Experimental Determination of Km, Vmax and Kcat Using Methyl Ester 9 and the Michaelis-Menten Equation To determine the characteristic values of our catalytic system, two hypotheses were made. As our system of catalysis is a gel supported on porous polymer foam contained in a reactor in a continuous flow system, the first hypothesis made is that the catalysis can be related to a packed bed reactor under continuous flow. The second is that the gel can be considered as a synzyme, which acts as a "Michaelian" enzyme during its steady state. Due to the catalyst and its confinement inside a reactor, a pre-steady state is observed. To determine the Km, Vmax and kcat, only the steady state is taken in account. The Michaelis-Menten equation describes the kinetic curve of $V_0$-[S]:

To determine Km and Vmax values, the Lineweaver-Burk graphical method was choosen. In order to plot the 1/V0 in function of 1/[S]$_0$, the $V_0$ values of the different concentration of substrate, were graphically determined by the slope present at the beginning of the steady state of the catalysis (after the inflection point) in the graph of the evolution of the product concentration as a function of time.

We obtained:

1/Vmax=0.0481 s/µmol=>Vmax=20.79 µmol/s
Km: Km/Vmax=1.35 s=>Km=1.35×20.79=28 mM

Then, it is possible to determine the kcat by using the following equation:

$$k_{cat} = \frac{V_{max}}{[enzyme]}$$

The hypothesis is that [enzyme]=["catalytic site" of the gel] (µmol/L). Then:

$$k_{cat} = \frac{V_{max}}{[enzyme]} = \frac{V_{max}}{[catalytic\ site\ of\ the\ hydrogel]} = \frac{20.79}{0.007} = 3 \times 10^3 s^{-1}$$

The concentration of catalytic site called [Enzyme] has been determined as following: the number of peptides involved in the catalytic process and present in our flow reactor (length 15 cm; diameter 4 mm) is 141 µmol (see Section 17 page 25). Considering the volume in the flow reactor, it represents a concentration [enzyme] 0.007 moles·L−1.

This example supports the enzyme-like activity of the gel.

Example 11— Enzymatic Activity of the Supported Supramolecular Hydrogel

The flow reactor has been prepared as described in Example 5. A solution of the phosphorylated model substrate, i.e. para-nitrophenylphosphate PNP, (8.2 mM in 20 mL of deionized water) is injected through the catalytic flow reactor using the flow rate value: 1.5 mL/min. The conversion of PNP in the product para-nitrophenol was monitored over time by HPLC analysis in order to evaluate the enzymatic activity of the alkaline phosphatase entrapped during the hydrogel formation. After 20 minutes, a complete conversion of PNP was observed. Then the flow reactor was extensively washed with deionized water and a second run was carried out using PNP solution in the same condition as described just above in the first run. The kinetic profile of this second run is similar to the one obtained for the first run, showing that no leaching of the enzyme occurs during these two runs without any loss of its activity.

The supported supramolecular hydrogel (on melamine) within the tubular column was stored at 4° C. after each run. Example 11 was repeated 30 times over 12 months. Kinetic profiles showing the conversion of PNP in para-nitrophenol of all runs overlap (FIG. 1). These results highlight the high stability of the enzymatic activity.

Example 12— Supramolecular Hydrogel Coating of Both the Tubular Column and all Pipes Used in the Flow Reactor (without the Foam Supported Hydrogel)

The whole interior surface of the tubular column and all pipes used in the flow reactor have been coated by the catalytic supramolecular hydrogel according to the protocol described in example 5. No open cell polymer foam has been used. Then a solution of the model ester substrate, i.e. para-nitrophenylacetate PNA, (1 mM in 20 mL of deionized water) is injected through the catalytic flow reactor using the flow rate value: 1.5 mL/min. The conversion of PNA in the product para-nitrophenol is monitored over time by HPLC analysis. Quasi no conversion of the substrate PNA is measured over time.

Figure 2:
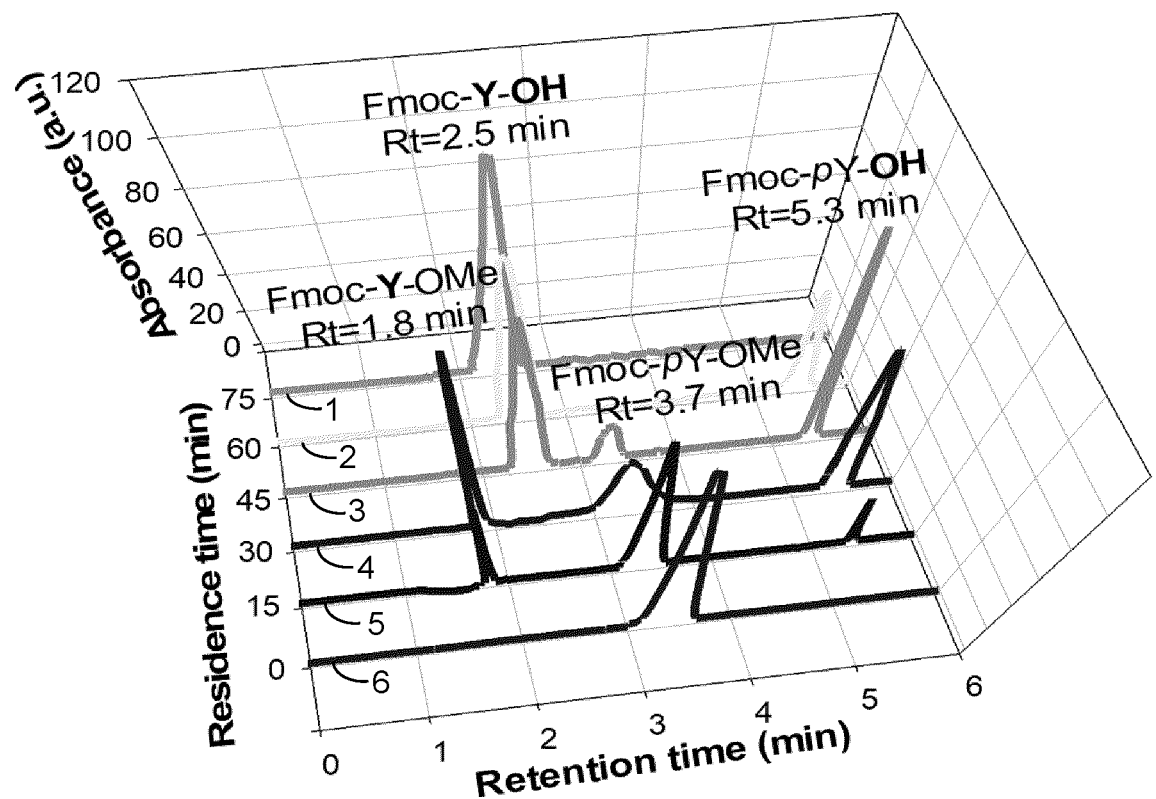
FIG. 2 represents a graphic illustrating that supported esterase-like hydrogel encapsulating AP allows to catalyze two reactions (phosphate and ester hydrolyses) on the same substrate Fmoc-pY-OMe, leading to Fmoc-Y—OH. HPLC monitoring has been done according to the residence time (example 13).
Figure 3:
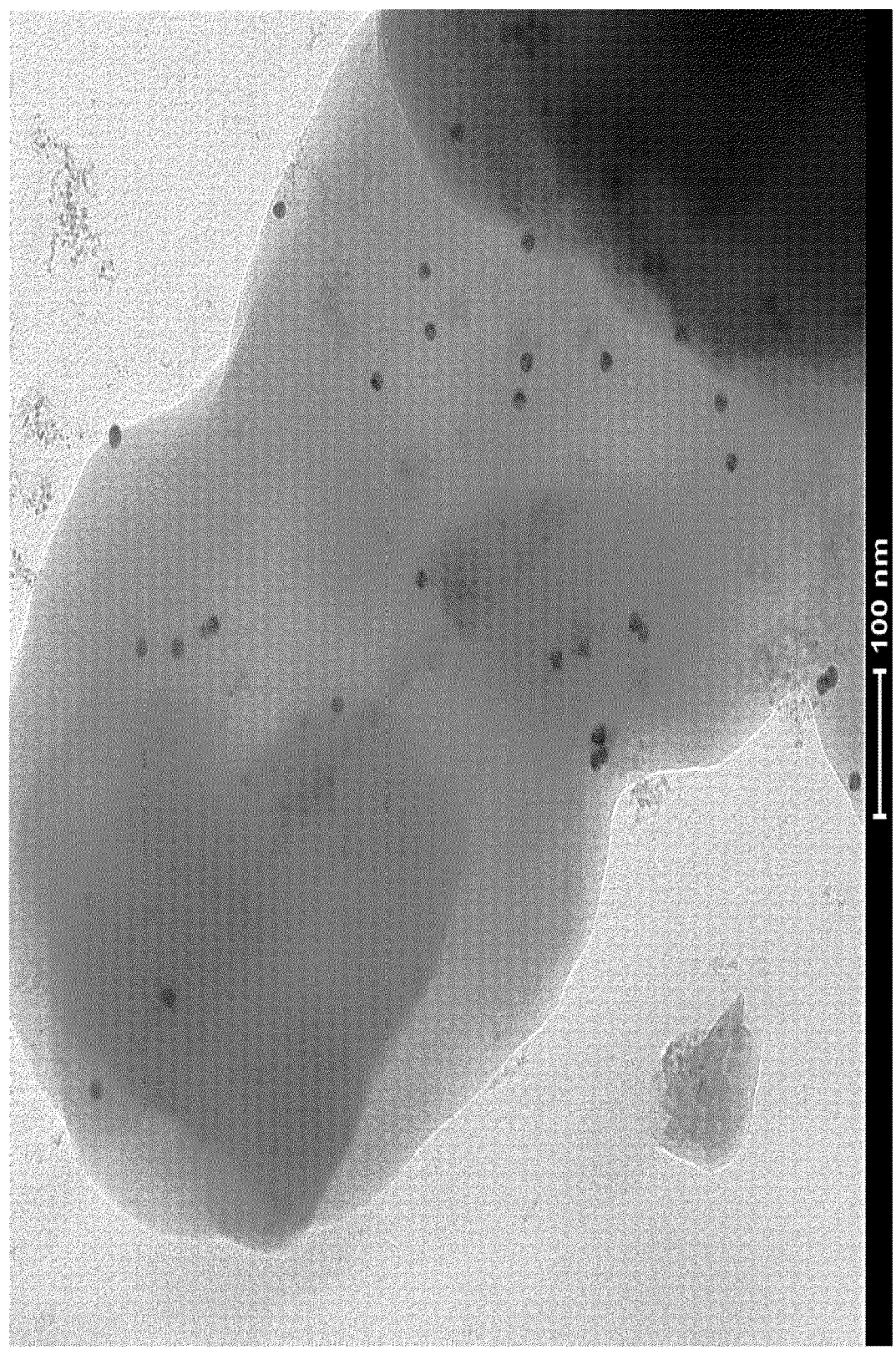
FIG. 3 represents a TEM image: piece of supramolecular hydrogel generated from melamine foam in presence of gold nanoparticles (diameter: 15 nm). The catalytically-active nanoojects (black dots) are encapsulated within the supramolecular hydrogel (example 14).

Example 13— Dual Enzymatic Activities Coming from Enzyme-Immobilized Hydrogel and Catalytic Peptide Self-Assembly The flow reactor has been prepared as described in Example 5 (using a melamine foam). The alkaline phosphatase (AP) used to trigger the hydrogel formation thus is encapsulated within the catalytic material. This means that two catalytic activities are present: an esterase-like activity coming from the peptide self-assembly and a phosphatase activity (enzymatic activity) coming from AP. A solution of N-Fmoc tyrosine phosphate methyl ester amino acid, Fmoc-pY-OMe, (5 mM is deionized water) is injected through the catalytic flow reactor using the flow rate value: 1.5 mL/min. The hydrolysis of both the phosphate group and the methyl ester group, leading to the product Fmoc-Y—OH, is monitored by HPLC (FIG. 2). This work shows the possibility to mix different kinds of catalyst within the same reactor for tandem or domino transformations.

Example 14: Encapsulation of Gold Nanoparticles (Θ=15 nm) within the Supported Supramolecular Hydrogel Supramolecular hydrogel was prepared according to example 5 using a solution of the phosphorylated tripeptide Fmoc-FFpY instead of Fmoc-GFFpYGHpY. The solution of the tripeptide Fmoc-FFpY was prepared by mixing a 10 mg/mL solution of Fmoc-FFpY with a 1OD gold nanoparticles solution in PBS purchased from Sigma-Aldrich (ref.: 777089) (1:1 v/v). Gold nanoparticles can be used as catalyst for various kind of chemical transformations. The resulting supported supramolecular hydrogel on melamine foam was red colored because of the presence of nanoparticles. After flowing PBS buffer through in a column (150*4.6 mm) for 16 h at a rate of 1 ml/min, the foam remained equally red TEM images of the gold nanoparticles-contained hydrogel shows the presence of nanoparticles within the gel at the micrometer scale (FIG. 3).

The invention claimed is:

1. A polymer foam, said polymer foam comprising pores forming an open-cell polymer foam, said polymer foam comprising a supramolecular gel inside the pores, and said polymer foam comprising at least one enzyme, wherein said supramolecular gel has at least one catalytic activity which is not provided by the enzyme but is provided by the supramolecular gel.

2. The polymer foam according to claim 1, wherein said supramolecular gel comprises nanofibers anchored on the surface of the pores of said polymer foam.

3. The polymer foam according to claim 1, wherein said supramolecular gel is a peptide-based hydrogel.

4. The polymer foam according to claim 1, wherein said supramolecular gel is an enzyme-assisted self-assembly gel.

5. The polymer foam according to claim 1, wherein said at least one enzyme is selected from the group consisting of esterase, phosphatase, alkaline phosphatase, β-lactamase, matrix metalloproteinase, matrix metalloproteinase-9 (MMP-9), chymotrypsin, thrombin, galactosidase, lipase, microbial transglutaminase (MTGase), thermolysin, glucose oxidase, peroxidase, tyrosinase, and any combination thereof.

6. The polymer foam according to claim 1, wherein said at least one catalytic activity is an esterase-like activity, or catalyzes a reaction selected from the group consisting of Aldolization, Mannich Reaction, Michael addition, hydrolysis of glycosidic bonds, Diels-Alder reaction in the presence of Cu(II) ions, oxidation of benzyl alcohol in the presence of Pd(II) ions, triazole formation by cycloaddition in the presence of Cu(I) ions, peroxidase activity in the presence of Fe(II) ions and a heme nucleus, $CO_2$ to carbonate conversion in the presence of Zn(II) ions and any combination thereof.

7. The polymer foam according to claim 1, wherein said polymer foam comprises a layer of polymer material forming a substrate and a layer of said supramolecular gel on said substrate, and wherein said at least one enzyme is adsorbed in said supramolecular gel.

8. The polymer foam according to claim 7, wherein said supramolecular gel comprises a polyelectrolyte multilayer comprising a combination of a polycationic compound and a polyanionic compound which form bilayers, said polyelectrolyte multilayer being in between the substrate and the supramolecular gel.

9. A method for preparing a polymer foam according to claim 1, said method comprising:
(a) providing a polymer foam comprising pores forming an open-cell polymer foam,
(b) providing an enzyme inside said pores of said polymer foam, and
(c) providing a molecule forming a supramolecular gel inside pores of said polymer foam.

10. The method of claim 9, wherein step (b) comprises coating said pores with a polyelectrolyte multilayer comprising a combination of a polycationic compound and a polyanionic compound which form bilayers prior to providing said enzyme and then coating said polyelectrolyte multilayer with said enzyme.

11. The method of claim 9, wherein the molecule forming said supramolecular gel is a peptide and step (c) further comprises growing the supramolecular gel inside the pores by enzymatic activity of said enzyme.

12. A flow reactor comprising a polymer foam according to claim 1.

13. A method for chemical synthesis comprising putting one or more chemical reactants in contact with a polymer foam according to claim 1, converting said one or more chemical reactants into one or more chemical products by a catalytic reaction performed by said polymer foam.

14. A method for kinetic resolution of chemical components comprising putting a mixture of chemical components in contact with a polymer foam according to claim 1, separating said mixture upon contact with said polymer foam and providing separated compounds from said mixture.

* * * * *